United States Patent
Govari et al.

(10) Patent No.: US 12,186,010 B2
(45) Date of Patent: Jan. 7, 2025

(54) WIRING FOR MULTI-ELECTRODE CATHETER

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Kevin Justin Herrera, West Covina, CA (US); Alexander David Squires, Duarte, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1021 days.

(21) Appl. No.: 16/584,740

(22) Filed: Sep. 26, 2019

(65) Prior Publication Data

US 2021/0093374 A1     Apr. 1, 2021

(51) Int. Cl.
*A61B 18/14*     (2006.01)
*A61B 5/00*     (2006.01)
(Continued)

(52) U.S. Cl.
CPC .......... *A61B 18/1492* (2013.01); *A61B 5/036* (2013.01); *A61B 5/287* (2021.01);
(Continued)

(58) Field of Classification Search
CPC ............ A61B 18/1492; A61B 18/1487; A61B 2018/00279; A61B 2018/144;
(Continued)

(56) References Cited

U.S. PATENT DOCUMENTS

| 5,391,199 A |   | 2/1995 | Ben-Haim |
| 5,491,299 A | * | 2/1996 | Naylor ................... A61B 5/303 |
|             |   |        | 174/105 R |

(Continued)

FOREIGN PATENT DOCUMENTS

| AU | 2015261572 A1 | 6/2016 |
| CA | 2987781 A1 | 6/2018 |

(Continued)

OTHER PUBLICATIONS

Extended European Search Report dated Jan. 26, 2021, from corresponding European Appl. No. 20198413.5.
(Continued)

*Primary Examiner* — Thomas A Giuliani

(57) ABSTRACT

In one embodiment, a catheter includes a shaft assembly having a proximal and distal end, which comprises a deflectable segment including lumens running longitudinally therein, electrodes disposed at the distal end, a connector disposed at the proximal end for coupling to processing circuitry, cables disposed in first respective ones of the lumens, each cable electrically coupled to the connector and a respective group of the electrodes, wherein each cable includes a bundle of wires, each wire connected to a respective one of the electrodes in the respective group, an electrical shielding surrounding the bundle, and an electrically insulating jacket surrounding the shielding and sized to allow longitudinal movement of the respective cable within the respective lumen, respective elongated members disposed in second respective ones of the lumens, and connected to the distal end, and a manipulator connected to the elongated members to actuate the distal end via the elongated members.

20 Claims, 5 Drawing Sheets

(51) Int. Cl.
*A61B 5/03* (2006.01)
*A61B 5/287* (2021.01)
*A61B 8/12* (2006.01)
*A61M 25/01* (2006.01)
*A61B 18/00* (2006.01)

(52) U.S. Cl.
CPC .............. *A61B 5/6852* (2013.01); *A61B 8/12* (2013.01); *A61M 25/0136* (2013.01); *A61B 2018/00351* (2013.01); *A61B 2018/1435* (2013.01)

(58) Field of Classification Search
CPC ...... A61B 2018/1415; A61B 2018/143; A61B 2018/1467; A61B 2018/00351; A61B 2018/1435; A61B 2018/00178; A61B 2018/00267; A61B 2018/1475; A61B 2018/00077; A61B 2018/00083; A61B 2018/00107; A61B 2018/0013; A61B 2018/00142; A61B 2018/0016; A61B 2018/00166; A61B 2018/00214
USPC ....... 606/32, 37, 39–41, 45–52; 607/98–101, 607/113–116
See application file for complete search history.

(56) References Cited

U.S. PATENT DOCUMENTS

| | | |
|---|---|---|
| 6,239,724 B1 | 5/2001 | Doron et al. |
| 6,254,568 B1 | 7/2001 | Ponzi |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 9,050,010 B2 | 6/2015 | Bui et al. |
| 9,492,228 B2* | 11/2016 | Lopes ................ A61B 18/00 |
| 11,305,092 B2* | 4/2022 | Leeflang ............ A61M 25/005 |
| 2002/0065455 A1 | 5/2002 | Ben-Haim et al. |
| 2003/0111255 A1* | 6/2003 | Buck .................. H01B 7/041 174/113 R |
| 2003/0120150 A1 | 6/2003 | Govari |
| 2004/0068178 A1 | 4/2004 | Govari |
| 2004/0193021 A1 | 9/2004 | Zdeblick et al. |
| 2005/0119650 A1* | 6/2005 | Sanders ............. A61B 18/1402 606/41 |
| 2006/0178030 A1 | 8/2006 | Lund et al. |
| 2009/0275838 A1 | 11/2009 | Marshall et al. |
| 2010/0063478 A1 | 3/2010 | Selkee |
| 2011/0077498 A1 | 3/2011 | McDaniel |
| 2012/0283570 A1 | 11/2012 | Tegg |
| 2014/0187893 A1* | 7/2014 | Clark ................ A61M 25/0009 606/41 |
| 2015/0080693 A1* | 3/2015 | Solis ................. A61B 18/1492 606/41 |
| 2015/0148877 A1* | 5/2015 | Thakkar ............ A61M 25/0147 607/116 |
| 2015/0272654 A1* | 10/2015 | Esch ................. A61B 18/1206 606/34 |
| 2015/0366508 A1* | 12/2015 | Chou ................... A61N 1/056 600/467 |
| 2018/0070845 A1 | 3/2018 | Hoitink et al. |
| 2019/0001143 A1 | 1/2019 | Sasaki |

FOREIGN PATENT DOCUMENTS

| | | |
|---|---|---|
| EP | 0 944 351 B1 | 3/2005 |
| JP | WO2005065559 A1 | 12/2007 |
| JP | 2011072782 A | 4/2011 |
| JP | WO2010113915 A1 | 10/2012 |
| JP | 2016511026 A | 4/2016 |
| JP | 2016537131 A | 12/2016 |
| JP | 2018094407 A | 6/2018 |
| WO | 1996005768 A1 | 2/1996 |
| WO | 96/41654 A1 | 12/1996 |
| WO | 1998014114 A1 | 4/1998 |

OTHER PUBLICATIONS

Examination Report dated Feb. 22, 2023, from corresponding European Appl. No. 20198413.5.
Xiao Kui Li et al: "Development of an Electrophysiology (EP)—Enabled Intracardiac Ultrasound Catheter Integrated With NavX 3-Dimensional Electrofield Mapping for Guiding Cardiac EP Interventions. Experimental Studies", Journal of Ultrasound in Medicine, American Institute for Ultrasound in Medicine, United States, vol. 26, Jan. 1, 2007 (Jan. 1, 2007), pp. 1565-1574, XP009134577, ISSN: 0278-4297.
Stephens D N et al: "The acoustic lens design and in vivo use of a multifunctional catheter combining intracardiac ultrasound imaging and electro physiology sensing", IEEE Transactions on Ultrasonics, Ferroelectrics, and Frequency Control, IEEE, USA, vol. 54, No. 3, Mar. 1, 2008 (Mar. 1, 2008), pp. 602-618, XP011206612, ISSN: 0885-3010.
Search Report dated Feb. 22, 2024, from corresponding Japanese Application No. 2020-160664.
Notice of Reasons for Refusal dated Feb. 27, 2024, from corresponding Japanese Application No. 2020-160664.
Written Opinion dated May 20, 2024, from corresponding Japanese Application No. 2020-160664.
Decision to Grant a Patent dated Jun. 4, 2024, from corresponding Japanese Application No. 2020-160664.

* cited by examiner

WIRING FOR MULTI-ELECTRODE CATHETER

FIELD OF THE INVENTION

The present invention relates to medical devices, and in particular, but not exclusively to, a multi-electrode catheter.

BACKGROUND

Electrode catheters have been in common use in medical practice for many years. They are used to stimulate and map electrical activity in the heart and to ablate sites of aberrant electrical activity. In use, the electrode catheter is inserted into a chamber of the heart. Once the catheter is positioned, the location of aberrant electrical activity within the heart is then located.

One location technique involves an electrophysiological mapping procedure whereby the electrical signals emanating from the conductive endocardial tissues are systematically monitored and a map is created of those signals. By analyzing that map, the physician can identify the interfering electrical pathway. A conventional method for mapping the electrical signals from conductive heart tissue is to percutaneously introduce an electrophysiology catheter (electrode catheter) having mapping electrodes mounted on its distal extremity. The catheter is maneuvered to place these electrodes in contact with or in close proximity to the endocardium. By monitoring the electrical signals at the endocardium, aberrant conductive tissue sites responsible for the arrhythmia can be pinpointed.

For mapping, it is desirable to have a relatively small mapping electrode. It has been found that smaller electrodes record more accurate and discrete electrograms. Additionally, if a bipolar mapping arrangement is used, it is desirable that the two electrodes of the mapping arrangement be in close proximity to each other and that they be similar in size to produce more accurate and useful electrograms.

Once the origination point for the arrhythmia has been located in the tissue, the physician uses an ablation procedure to destroy the tissue causing the arrhythmia in an attempt to remove the electrical signal irregularities and restore normal heart beat or at least an improved heartbeat. Successful ablation of the conductive tissue at the arrhythmia initiation site usually terminates the arrhythmia or at least moderates the heart rhythm to acceptable levels.

Multi-electrode catheters come in various forms, including, flower catheters, balloon catheters and basket catheters, by way of example only. Some of the catheters may have tens of electrodes and some in excess of one-hundred electrodes. These multi-electrode catheters help streamline and speedup the mapping or ablation procedure. However, as the number of electrodes increases so does the complexity of coupling the electrodes with a control unit of the catheter via a catheter shaft, which has limited dimensions due to the inherent limited size of the blood vessels through which the catheter must traverse.

US Patent Publication 2004/0193021 of Zdeblick, et al., describes a multiplexed medical carrier which provides for sensing one or more patient parameters and/or delivering energy via separately identifiable effectors. The carrier includes a body and at least two electrical conductors coupled with at least two effectors. Effectors may be any combination of sensors, actuators or both. Sensors may measure such parameters as pressure, oxygen content, volume, conductivity, fluid flow rate, or any other chemical or physical parameters. Actuators may be used, for example, to pace a heart, stimulate muscle or neural tissue, broadcast ultrasonic energy, emit light, heat or other forms of radiation, or deliver any form of energy or substance.

PCT Patent Publication WO1998/014114 of Edwards Lifesciences Corporation, describes a catheter including a body portion having a distal end and a proximal end. A plurality of lumens is formed in the body portion between the distal and proximal ends. A heating element and a temperature sensor are disposed on the catheter, with the temperature sensor being positioned between the heating element and the distal end of the body portion. Heating-element wires are connected to the heating element and extend from the heating element to the proximal end of the body portion in one of the lumens of the catheter, and temperature-sensor wires are connected to the temperature sensor and extend in a twisted configuration from the temperature sensor to the proximal end of the body portion in one of the lumens of the catheter. The heating-element wires are connectable to a control unit and carry an activation signal from the control unit to the heating element to activate the heating element. The temperature-sensor wires are connectable to a processing unit and carry a temperature-sensor signal from the temperature sensor to the processing unit for processing.

US Patent Publication 2009/0275838 of Marshall, et al., describes a catheter assembly for an intravascular ultrasound system includes a catheter, an imaging core, and a shield-coupling capacitor. The catheter defines a lumen extending along a longitudinal length of the catheter. The imaging core is configured and arranged for inserting into the lumen. The imaging core includes a rotatable driveshaft, one or more transducers, one or more conductors, and a conductive shield. The one or more transducers are mounted to the rotatable driveshaft. The one or more conductors are coupled to the one or more transducers and extend along the driveshaft. The conductive shield is disposed around the one or more conductors. The shield-coupling capacitor is electrically coupled to the conductive shield and includes one or more rotating capacitors. The one or more rotating capacitors include one or more rotating plates and one or more stationary plates. The shield-coupling capacitor is configured and arranged for coupling to a system ground.

US Patent Publication 2010/0063478 of Selkee describes a force-sensing catheter for diagnosing or treating the vessels found within a body or body space includes a center strut that is bonded, preferably thermally, along its longitudinal axis with the thermoplastic tubular member within which it is housed. The tubular member preferably has three layers: an inner layer, a braided layer and an outer layer. One or more semiconductor or metallic foil strain gauges are affixed to the center strut in order to provide a measure of the bending and torsional forces on the distal tip of the catheter. Temperature compensation is achieved by having a temperature sensor near the strain gauges and calibrating the catheter over a range of temperatures.

SUMMARY

There is provided in accordance with an embodiment of the present disclosure, a catheter configured to be inserted into a body part of a living subject, and including a shaft assembly having a proximal end and a distal end, which includes a deflectable segment including lumens running longitudinally in the deflectable segment, multiple electrodes disposed at the distal end of the shaft assembly, a connector disposed at the proximal end of the shaft assembly for coupling to processing circuitry, a plurality of cables disposed in first respective ones of the lumens, each cable electrically coupled to the connector and a respective group of the electrodes, wherein each cable includes a bundle of individually insulated wires, each wire connected to a respective one of the electrodes in the respective group, an electrical shielding surrounding the bundle, and an electrically insulating jacket surrounding the electrical shielding and sized to allow longitudinal movement of the respective cable within the respective lumen, respective elongated members disposed in second respective ones of the lumens, and connected to the distal end, and a manipulator connected to the elongated members and configured to actuate the distal end via the elongated members.

Further in accordance with an embodiment of the present disclosure the manipulator is configured to change an orientation of the deflectable segment via at least one of the elongated members.

Still further in accordance with an embodiment of the present disclosure the distal end includes an assembly on which the multiple electrodes are disposed, at least one of the elongated members being coupled to the assembly, the manipulator being configured to deploy the assembly via the at least one elongated member.

Additionally, in accordance with an embodiment of the present disclosure the catheter includes two respective resilient elongated members disposed in third respective ones of the lumens, the two resilient elongated members defining a plane of preferential bending of the deflectable segment.

Moreover, in accordance with an embodiment of the present disclosure the deflectable segment has an outside diameter of less than 3 mm.

Further in accordance with an embodiment of the present disclosure each of the cables has an outside diameter of less than 0.5 mm and includes at least twenty insulated wires.

Still further in accordance with an embodiment of the present disclosure the catheter includes at least three of the cables.

Additionally, in accordance with an embodiment of the present disclosure each of the cables has an outside diameter of less than 0.

5 mm and includes at least thirty insulated wires.

Moreover, in accordance with an embodiment of the present disclosure the catheter includes at least three of the cables.

Further in accordance with an embodiment of the present disclosure each respective cable includes tape which is wrapped around the bundle of insulated wires underneath the shielding.

Still further in accordance with an embodiment of the present disclosure the electrically insulating jacket includes any one or more of the following polytetrafluoroethylene (PTFE), or perfluoroalkoxy alkane (PFA).

Additionally, in accordance with an embodiment of the present disclosure the deflectable segment includes a thermoplastic elastomer.

Moreover, in accordance with an embodiment of the present disclosure the electrical shielding includes a non-overlapping wire spiral.

Further in accordance with an embodiment of the present disclosure the electrical shielding includes a tinned-copper alloy.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
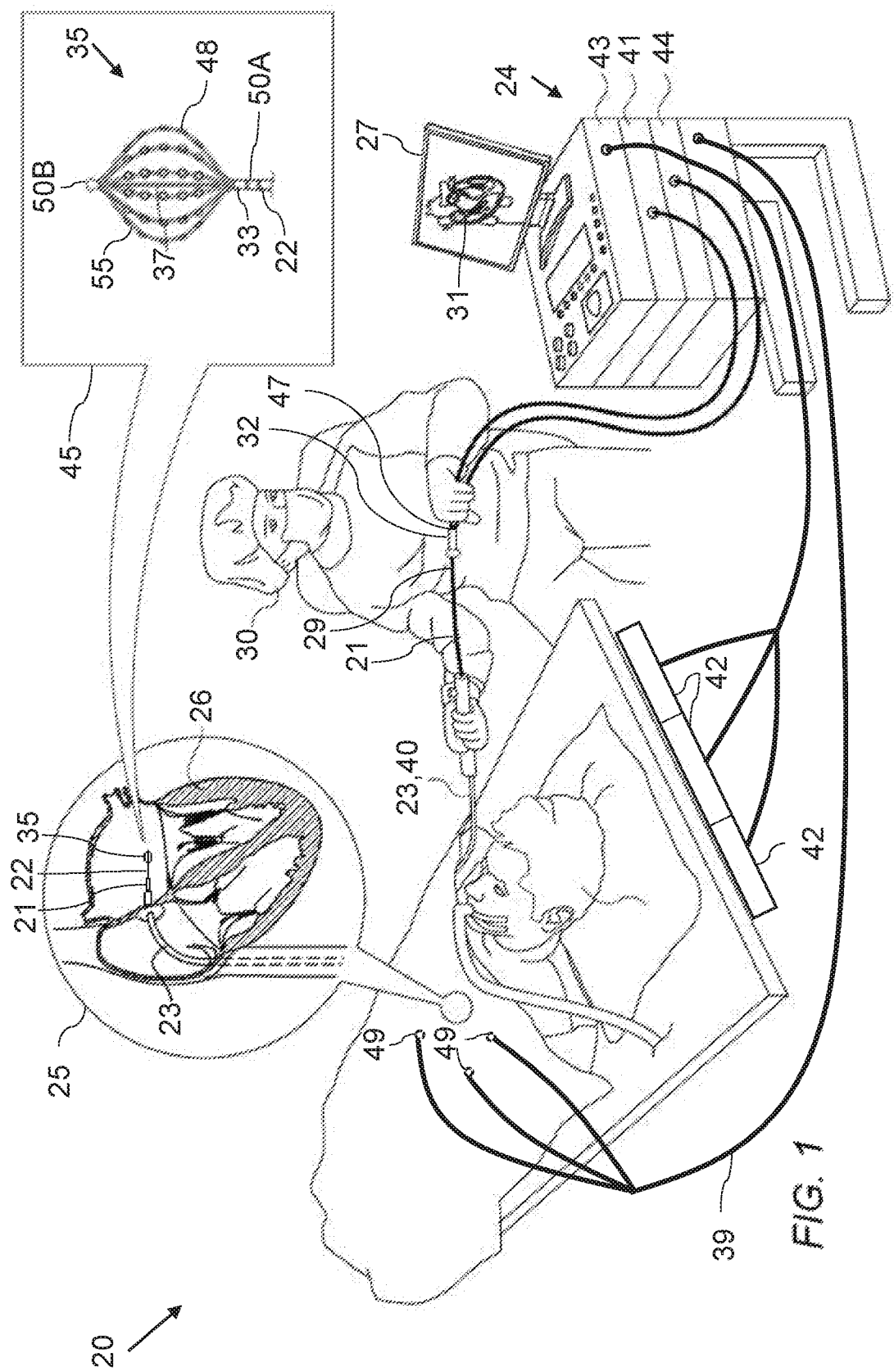
FIG. 1 is a schematic, pictorial illustration of a system for electro-anatomical mapping comprising a catheter, in accordance with an embodiment of the present invention.

As previously discussed, multi-electrode catheters come in various forms, including, flower catheters, balloon catheters and basket catheters, by way of example only. Some of the catheters may have tens of electrodes and some in excess of one hundred electrodes. These multi-electrode catheters help streamline and speedup the mapping or ablation procedure. However, as the number of electrodes increases so does the complexity of coupling the electrodes with a control unit of the catheter via a catheter shaft assembly, which has limited dimensions due to the inherent limited size of the blood vessels through which the catheter must traverse. Additionally, if the interior components of the catheter shaft assembly are too thick, the shaft assembly may not have the required flexibility it needs to traverse the blood vessels even if the shaft assembly itself is narrower than the blood vessels.

Compounding the complexity of coupling the electrodes to the control unit via the catheter shaft assembly is the presence of other items in the shaft assembly such as mechanical elements for controlling the deflection of a deflectable segment of the distal end of the shaft assembly, and/or deploying and controlling a distal end assembly, such as a basket or balloon, on which the electrodes are disposed. Other elements such as irrigation tubing may also be disposed in the shaft assembly.

Another problem associated with coupling the electrodes to the control unit is that as the catheter deflects, electrical noise due to electrostatic discharge from the insulation of the wires is generated on the wires coupling the electrodes to the control unit. Since the electrical activity sensed by the electrodes is in the order of millivolts with microvolt resolution, the noise generated in the wires may significantly impact the accuracy of the sensed electrical activity.

An additional problem associated with coupling the electrodes to the control unit is that the wires need a certain amount of freedom of motion within the deflectable segment, as otherwise the wires may break when the deflectable segment is deflected. Therefore, the wires require space in the deflectable segment to provide this freedom of motion.

As mentioned above the available space in the deflectable segment is used for many items and the maximum outside diameter of the shaft assembly is also limited. In addition, the deflectable element itself cannot be a hollow shell to accommodate all the required items as it needs to have a sufficient amount of structure in order to provide support for the elements it contains as well as for pushing the catheter through the blood vessels.

Embodiments of the present invention solve the above problems by providing a catheter with a shaft assembly having a deflectable segment with a plurality of lumens disposed longitudinally in the deflectable segment. The deflectable segment has a maximum diameter (for example, 3 mm), which allows the deflectable segment to fit in the blood vessels it was designed to traverse, as well as giving the deflectable segment the flexibility it needs to traverse those blood vessels. In some embodiments, the diameter of the deflectable segment is 2.67 mm or less.

The size and number of lumens are limited to ensure that the deflectable segment is strong enough to support the elements it contains (e.g., mechanical elements for controlling the deflection of the deflectable segment, and/or deploying and controlling a distal end assembly, such as a basket or balloon, on which electrodes are disposed) and to be guided successfully through the blood vessels.

The electrodes disposed at the distal end are coupled to a console via multiple electrically-shielded cables, each cable serving a group of electrodes, and each cable being disposed in a respective one of the lumens, while mechanical and other elements are disposed in other lumens. Each cable is electrically coupled to a connector (which reversibly connects to the console) and a respective group of the electrodes. Each cable includes a bundle of individually insulated wires with each wire being connected to a respective one of the electrodes in the respective group. Disposing the cables and mechanical elements in separate lumens allows the mechanical elements to operate freely and helps isolate the cables from problematic static that would be caused by movement of the mechanical elements.

Dividing the electrode wires among multiple cables may at first appear to be counterintuitive, as a single cable generally has a smaller cross-sectional area than the combined cross-sectional areas of separate cables. However, dividing the wires connecting the electrodes with the console into multiple cables provides a greater mechanical flexibility than a single larger cable and provides an overall packing efficiency which allows space for the mechanical elements and the wires subject to the structural limits of the deflectable segment mentioned above.

The deflectable segment may include any suitable number of lumens of any suitable size. In some embodiments, the deflectable segment includes a central lumen surrounded by eight peripheral lumens. The central lumen may have any suitable diameter, and in example embodiments has a diameter of about 1 mm. The peripheral lumens may have any suitable diameter, and in example embodiments each of the peripheral lumens has a diameter of about 0.56 mm. The central lumen may contain a mechanical element for deploying and controlling the distal end assembly, such as a basket or balloon. In other embodiments, the central lumen may be reserved for another element or elements, for example, but not limited to, irrigation tubing, other wiring, and/or optic cables. Two of the peripheral lumens may each include a resilient elongated member, for example, resilient tubes. The two resilient elongated members define a plane of preferential bending of the deflectable segment. Another two of the peripheral lumens may include mechanical elements (such as rods or wires) for controlling the deflection of the deflectable segment at the distal end of the shaft.

The remaining peripheral lumens may be used for routing four electrically shielded cables. Each of the cables may include insulated wires bound together with a plastic tape, which is surrounded with an electrical shielding, which is in turn surrounded with an insulated jacket. Each of the cables may include any suitable number of insulated wires. In some embodiments, each cable includes thirty insulated wires so that four cables may in total connect 120 electrodes disposed at the distal end with the console via the shaft assembly. Each cable may have any suitable outer diameter to allow the cable sufficient freedom of movement in its lumen so that when the deflectable segment is deflected the insulated wires do not break. In example embodiments, the outer diameter of the cable may be 0.4 to 0.5 mm.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Reference is now made to FIG. 1, which is a schematic, pictorial illustration of an electro-anatomical medical mapping system 20, in accordance with an embodiment of the present invention. The electro-anatomical mapping system 20 includes a catheter 40 configured to be inserted into a body part of a living subject (e.g., a patient 28). A physician 30 navigates the catheter 40 (for example, a basket catheter produced Biosense Webster, Inc. of Irvine, CA, USA), seen in detail in inset 45, to a target location in a heart 26 of the patient 28. The catheter 40 includes a shaft assembly 21 having a proximal end 29 and a distal end 33. The distal end 33 include the deflectable segment 22. The physician 30 navigates the catheter 40 by manipulating the deflectable segment 22 of the catheter 40, using a manipulator 32 near the proximal end 29 of the shaft assembly 21, and/or deflection from a sheath 23. In the embodiment seen in inset 25, physician 30 uses catheter 40 to perform electro-anatomical mapping of a cardiac chamber.

The catheter 40 includes multiple electrodes 48 disposed at the distal end 33. In some embodiments, the distal end 33 of the shaft assembly 21 includes an assembly 35 (e.g., a basket assembly) on which the electrodes 48 are disposed. The catheter 40 includes an elongated member 37 coupled to the assembly close to a sensor 50B, described in more detail below. The elongated member 37 is typically a tube that is disposed in a lumen of the deflectable segment. The elongated member 37 is generally controlled via the manipulator 32 to deploy the assembly 35 and change an ellipticity of the assembly 35 according to the longitudinal displacement of the elongated member 37 with respect to the deflectable segment. The elongated member 37 is described in more detail with reference to FIGS. 3-5.

Embodiments described herein refer mainly to a basket distal-end assembly 35, purely by way of example. In alternative embodiments, the disclosed techniques can be used with a catheter having a balloon-based distal-end assembly or of any other suitable type of distal-end assembly, such as a flower-type distal end assembly, for example, but not limited to, based on a Pentaray® or Octaray® catheter produced by Biosense Webster, Inc.

Catheter 40 is inserted in a folded configuration, through sheath 23, and only after the catheter 40 exits sheath 23 does catheter 40 regain its intended functional shape. By containing catheter 40 in a folded configuration, sheath 23 also serves to minimize vascular trauma on its way to the target location.

Catheter 40 may incorporate a magnetic sensor 50A, seen in inset 45, at the distal edge of the deflectable segment 22 (i.e., at the proximal edge of basket assembly 35). Typically, although not necessarily, sensor 50A is a Triple-Axis Sensor (TAS). A second magnetic sensor 50B may be included in a distal edge of the basket assembly 35. Sensor 50B may be a Single-Axis Sensor (SAS), Double-Axis Sensor (DAS), or a Triple-Axis Sensor (TAS), by way of example only.

The assembly 35 further comprises multiple expandable spines 55, which may be mechanically flexible, to each of which are coupled the electrodes 48. The assembly 35 may include any suitable number of electrodes 48. In some embodiments, the assembly 35 may include ten spines 55 and 120 electrodes, with 12 electrodes disposed on each spine 55. First ends of the spines 55 are connected to the distal end of the shaft assembly 21 and second ends of the spines 55 are connected to the distal end of the elongated member 37.

The actual basket assembly 35 structure may vary. For example, expandable spines 55 may be made of a printed circuit board (PCB), or of a shape-memory alloy. Magnetic sensors 50A and 50B and electrodes 48 are connected by wires running through shaft assembly 21 to various driver circuitries in a console 24. The wiring is discussed in more detail with reference to FIGS. 3-5.

In some embodiments, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance between sensors 50A and 50B. Patient 28 is placed in a magnetic field generated by a pad containing magnetic field generator coils 42, which are driven by a unit 43. The magnetic fields generated by coils 42 generate signals in sensors 50A and 50B, which are indicative of position and/or direction. The generated signals are transmitted to console 24 and become corresponding electrical inputs to processing circuitry 41. The processing circuitry 41 uses the signals to calculate the elongation of the basket assembly 35, and to estimate basket ellipticity and elongation/retraction state from the calculated distance between sensors 50A and 50B.

The method of position and/or direction sensing using external magnetic fields and magnetic sensors, such as 50A and 50B, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processing circuitry 41, typically part of a general-purpose computer, is further connected via a suitable front end and interface circuits 44, to receive signals from surface-electrodes 49. Processing circuitry 41 is connected to surface-electrodes 49 by wires running through a cable 39 to the chest of patient 28.

The catheter 40 includes a connector 47 disposed at the proximal end 29 of the manipulator 32 for coupling to the processing circuitry 41.

In an embodiment, processing circuitry 41 additionally receives various spatial and electrophysiological signals from the electrodes 48 via interface circuits 44, and generates an electroanatomic map 31 of the cavity responsively to information contained in these signals. During and/or following the procedure, processing circuitry 41 may display the electro-anatomical map 31 on a display 27.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Figure 2:
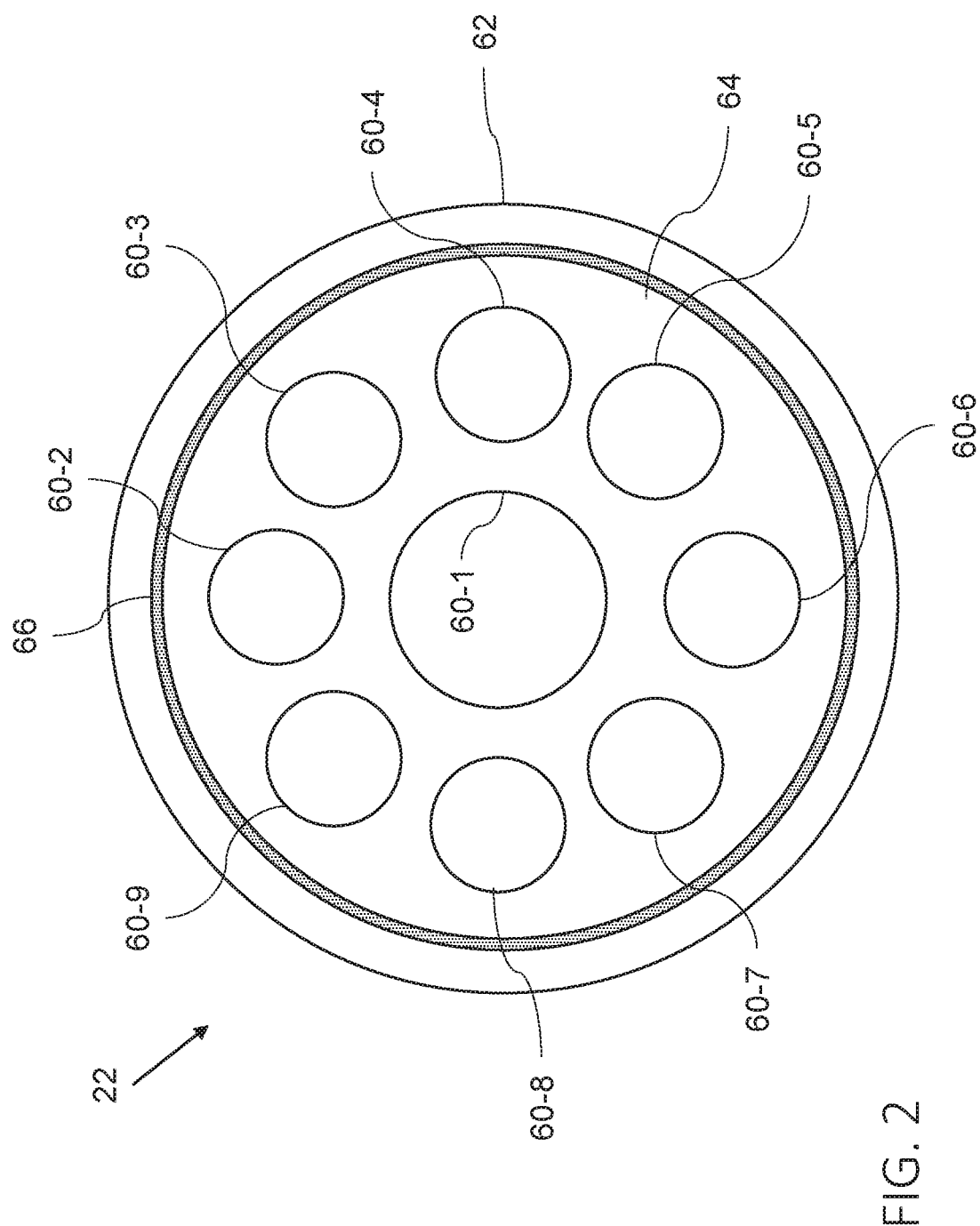
FIG. 2 is a transverse cross-sectional view of a deflectable segment of the catheter of FIG. 1.

Reference is now made to FIG. 2, which is a transverse cross-sectional view of the deflectable segment 22 of the catheter 40 of FIG. 1.

The deflectable segment 22 includes lumens 60 running longitudinally in therein. In some embodiments the deflectable segment 22 is made from an outer portion 62 and an inner portion 64 separated by a braiding layer 66. The inner portion 64 includes the lumens 60 disposed therein. The braiding layer 66 serves to provide torque transfer between the proximal end 29 and the distal end 33 of the catheter 40. In other embodiments, the deflectable segment 22 is formed as a single portion without the braiding layer 66.

The outer portion 62 and the inner portion 64 may be formed from any suitable biocompatible material, for example, a flexible biocompatible plastic or the like. In some embodiments, the outer portion 62 and the inner portion 64 may be formed from 80% polyether block amide (PEBA) and 20% BaSO4 (barium sulfate). The braiding layer 66 may be any suitable wire for example, but not limited to, a flat wire braid. The braiding layer 66 may have any suitable dimensions. In example embodiments, the braiding layer 66 has an inner diameter of 2.34 mm and a thickness of 0.076 mm. The deflectable segment 22 generally has an outside diameter of less than 3 mm. In example embodiments the deflectable segment 22 has an outside diameter of 2.67 mm.

The deflectable segment 22 may include any suitable number of the lumens 60. Additionally, the lumens 60 may have any suitable size and be arranged in the deflectable segment 22 according to any suitable arrangement. The lumens 60 shown in FIG. 2 include a central lumen 60 surrounded by eight smaller lumens 60. This particular arrangement may be useful when a larger lumen 60 is needed for one or more elements. In an example embodiment, the central lumen 60 has a diameter of about 1 mm and the other lumens 60 have a diameter of about 0.56 mm.

Figure 3:
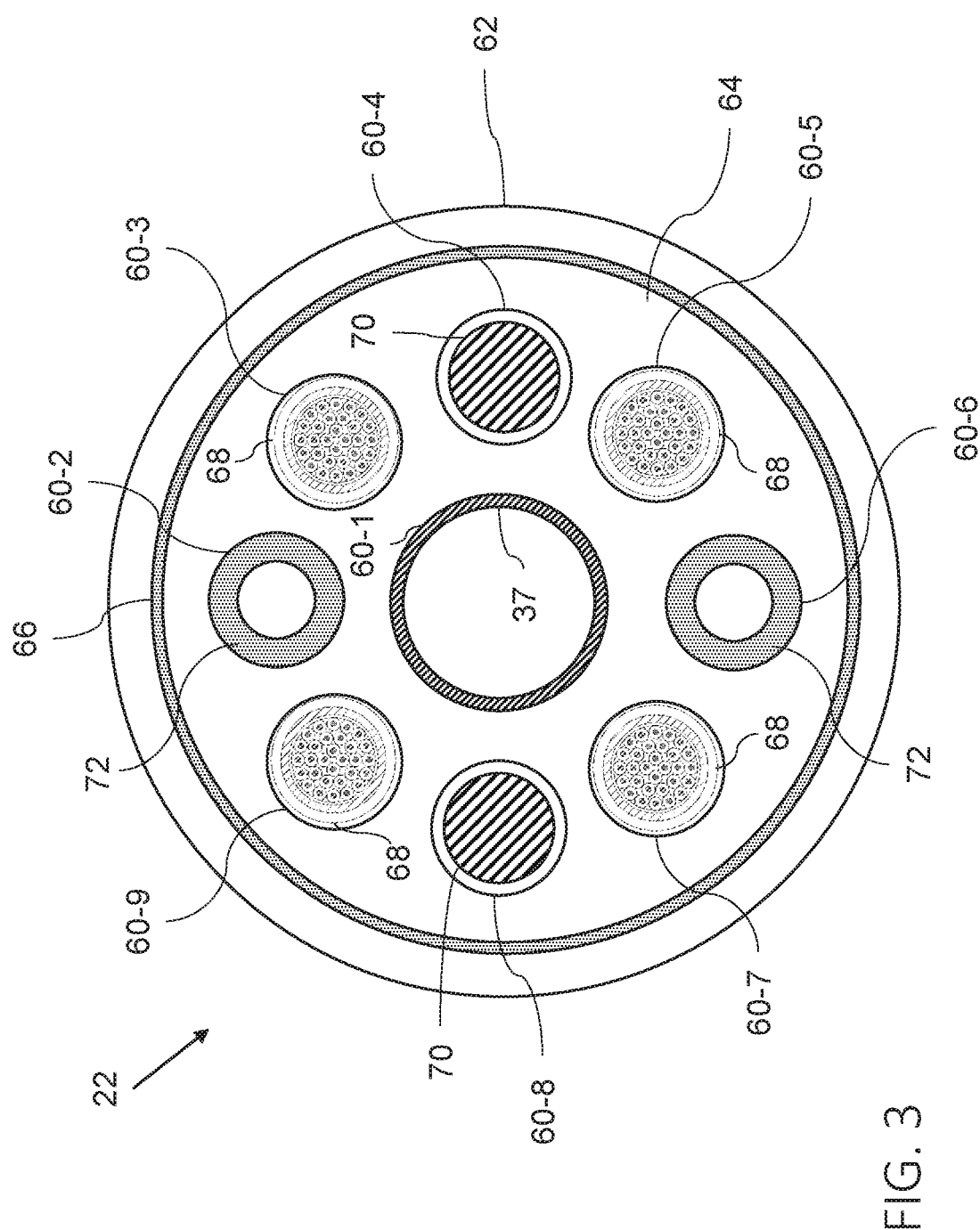
FIG. 3 is a transverse cross-sectional view of the deflectable segment of FIG. 1 with its lumens loaded.

Reference is now made to FIG. 3, which is a transverse cross-sectional view of the deflectable segment 22 of FIG. 2 with its lumens loaded with various elements. The catheter 40 includes a plurality of cables 68 with respective cables 68 disposed in respective ones of the lumens 60-3, 60-5, 60-7, 60-9. Each cable 68 is electrically coupled to the connector 47 (FIG. 1) and a respective group of the electrodes 48 (FIG. 1). In some embodiments, the outside diameter of the cables 68 is less than 0.5 mm. The cables 68 are described in more detail with reference to FIG. 5. FIG. 3 shows four cables disposed in the lumens 60. In some embodiments, the catheter 40 may include two, three or even more than four cables 68 disposed in the lumens 60.

In some embodiments, the catheter 40 includes the elongated member 37 disposed in the lumen 60-1, and respective elongated members 70 disposed in respective ones of the lumens 60-2, 60-6. The elongated members 37, 70 are connected to the distal end 33 of the shaft assembly 21 and to the manipulator 32 (FIG. 1), which is configured to actuate the distal end 33 via the elongated members 37, 70, as described in more detail below.

The manipulator 32 is configured to deploy and adjust the assembly 35 (FIG. 1) of the catheter 40 via the elongated member 37, by moving the elongated member 37 longitudinally with respect to the deflectable segment 22. In some embodiments, the elongated member 37 may be a tube or rod comprised of any suitable material and having any suitable diameter and thickness. In example embodiments, the elongated member 37 is formed from a polyimide tube having an outside diameter of approximately 1 mm.

The manipulator 32 is configured to change an orientation of the deflectable segment 22 of the distal end 33 via at least one of the elongated members 70. The elongated members 70 are generally connected to the distal end 33 (e.g., to the distal end of the deflectable segment 22) so that pulling or pushing the elongated members 70 with the manipulator 32 deflects the deflectable segment 22 sideways. The catheter 40 may include more than two elongated members 70 in order to provide greater control of the deflection of the deflectable segment 22. In some embodiments, each elongated member 70 may be a tube, rod or wire comprised of any suitable material and having any suitable diameter and thickness. In some embodiments, in a proximal region of the deflectable segment 22, each elongated member 70 is surrounded with a compression coil which is secured to the deflectable segment 22 in a compressed state. When the elongated member 70 is pulled, the compression coil resists compression in the deflectable segment 22 and prevents the deflectable segment 22 from becoming too wavy or floppy. In example embodiments, each elongated member 70 is formed from stainless steel or any other suitable material, with an outside diameter of approximately 0.18 mm. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. The catheter 40 comprises two respective resilient elongated members 72 disposed in respective ones of the lumens 60-2, 60-6. The two resilient elongated members 72 define a plane of preferential bending of the deflectable segment 22. In example embodiments, the elongated members 72 are formed from polyamide, such as VESTAMID® CARE of Evonik Resource Efficiency GmbH of Essen Germany with an inside diameter of 0.3 mm, and an outside diameter of 0.56 mm. In other embodiments, the elongated members 72 may be formed from any other suitable material, for example, polyimide, Polyether Ether Ketone (PEEK), or Polyethersulfone (PESU). One example of a handle for use as manipulator 32 can be found in U.S. Pat. No. 9,050,010 as well as the handle described and illustrated in U.S. Provisional Patent Application Ser. No. 62/903,337 (BIO6216USPSP1) filed on Sep. 20, 2019, all incorporated by reference with a copy provided in the Appendix.

In other embodiments, the lumens 60-1, 60-2, 60-4, 60-6, 60-8 may include any suitable elements for example, but not limited to irrigation tubes and/or optical fibers.

Figure 4:
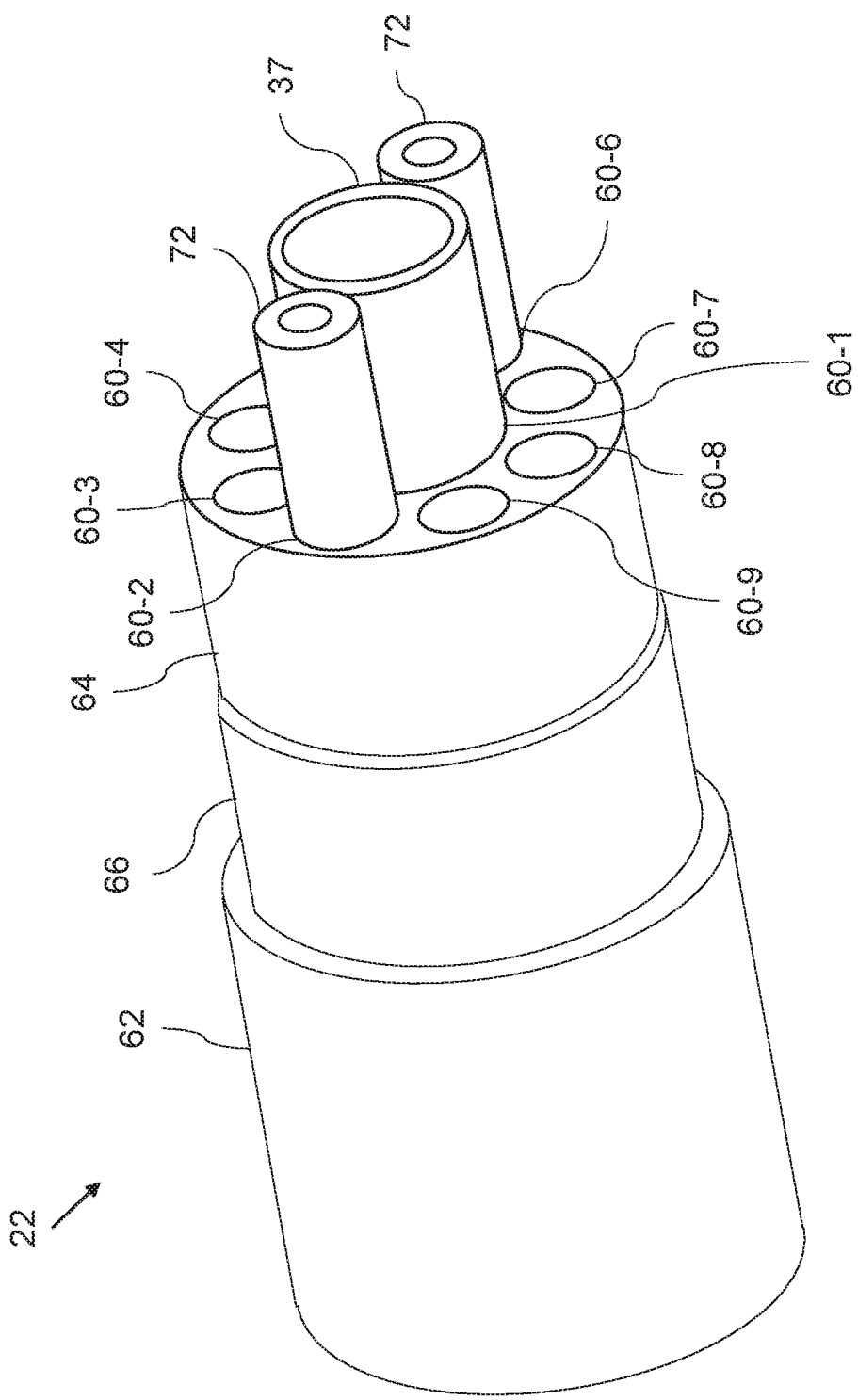
FIG. 4 is a cutaway view of the deflectable segment of the catheter of FIG. 1.

FIG. 4 is a cutaway view of the deflectable segment 22 of the catheter 40 of FIG. 1. FIG. 4 shows the lumens 60 of the deflectable segment 22 loaded with the elongated member 37 and the elongated members 72. FIG. 4 does not show the cables 68 or the elongated members 70.

Figure 5:
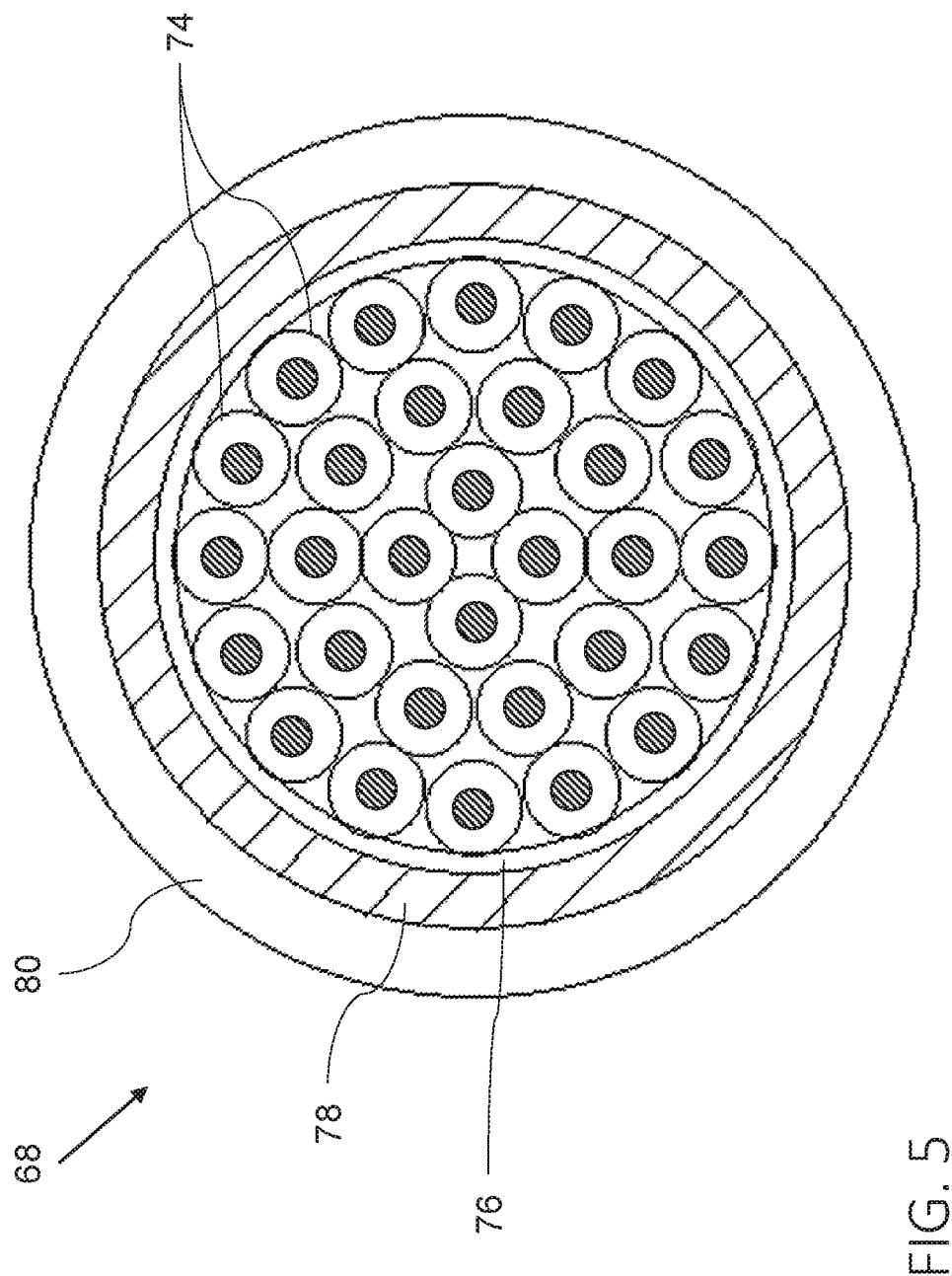
FIG. 5 is a cross-sectional view of one of the cables included in the deflectable segment of FIG. 3.

Reference is now made to FIG. 5, which is a cross-sectional view of one of the cables 68 included in the deflectable segment 22 of FIG. 3.

Each cable 68 includes a bundle of (e.g., at least 20 or 30) individually insulated wires 74 (only some of the wires 74 have been labeled for the sake of simplicity). As mentioned above with reference to FIG. 3, each cable 68 is electrically coupled to the connector 47 (FIG. 1) and a respective group of the electrodes 48 (FIG. 1). Each wire 74 is connected to a respective one of the electrodes 48 in the respective group. The conductor of the wires 74 may be formed from any suitable conducting material, for example, but not limited to, copper alloy wire. In example embodiments the outside diameter of the conductor is 0.032 mm. The insulator of the wires 74 may be formed from any suitable material, for example, but not limited to polyurethane, polyimide, or any thin enamel insulation. In example embodiments the insulator has an outside diameter of 0.042 mm. If the catheter 40 includes 120 electrodes 48, the catheter 40 typically includes four cables, with each cable including thirty wires 74. For an Octaray catheter with 50 electrodes, the catheter 40 include two cables 68, with each cable including twenty-five wires 74. Insulated wires connecting the sensors 50 to the processing circuitry 41 may also be included in one or more of the cables 68.

Each cable 68 includes tape 76 (e.g., plastic tape) which is wrapped around the bundle of insulated wires 74 underneath a shielding 78 (described below). The tape 76 holds the bundle of wires 74 together and adds a barrier between the wires 74 and the shielding 78, which could damage the insulators of the wires 74.

Each cable 68 includes the electrical shielding 78 surrounding the bundle and tape 76. The shielding 78 sheds electrostatic charges. The electrical shielding 78 may comprise any suitable shielding material. In some embodiments, the shielding 78 comprises a non-overlapping wire spiral of a tinned-copper alloy with a thickness of about 0.025 mm.

Each cable 68 also includes an electrically insulating jacket 80 surrounding the electrical shielding 78 and is sized to allow longitudinal movement of the respective cable 68 within the respective lumen 60 (FIGS. 2-4). The electrically insulating jacket 80 may includes any one or more of the following by way of example only: polytetrafluoroethylene (PTFE); or perfluoro alkoxy alkane (PFA) for smooth sliding of the cables 68 in the lumens 60. In example embodiments, the electrically insulating jacket 80 has an outside diameter of about 0.4 mm and a thickness of about 0.03 mm. The electrically insulating jacket 80 functions to hold the shield 78 together so that the shielding 78 does not bunch up when the cable 68 slides back and forth in the lumen 60. The cables 68 slide in the lumen 60 but may be fixed at the distal end of the deflectable segment 22.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A catheter configured to be inserted into a body part of a living subject, and comprising:
   a shaft assembly having a proximal end and a distal end, the shaft assembly extending along a longitudinal axis and comprising:
      a deflectable segment including lumens running longitudinally in the deflectable segment;
      an inner portion and an outer portion, the inner portion comprising the lumens and the outer portion disposed around an outer circumference of the inner portion; and
      a braiding layer disposed between the inner portion and the outer portion; and
   an expandable distal end assembly comprising a plurality of spines configured to bow radially outward from the longitudinal axis, each spine of the plurality of spines comprising a flexible printed circuit board comprising multiple electrodes disposed along the spine, the expandable distal end assembly configured to transition between an expanded configuration and a collapsed configuration;
   a connector disposed at the proximal end of the shaft assembly for coupling to processing circuitry;
   a plurality of cables disposed in first respective ones of the lumens, each cable of the plurality of cables electrically coupled to the connector and a respective group of the multiple electrodes, wherein each cable of the plurality of cables comprises:
      a bundle of individually insulated wires, each wire of the individually insulated wires connected to a respective electrode of the multiple electrodes in the respective group;
      an electrical shielding surrounding the bundle and extending from the proximal end to the distal end of the shaft assembly; and
      an electrically insulating jacket surrounding the electrical shielding and sized to allow longitudinal movement of the respective cable within the respective lumen;
   respective elongated members disposed in second respective ones of the lumens, and connected to the distal end; and
   a manipulator connected to the elongated members and configured to actuate the distal end via the elongated members.

2. The catheter according to claim 1, wherein the manipulator is configured to change an orientation of the deflectable segment via at least one of the elongated members.

3. The catheter according to claim 2, wherein the catheter comprises two respective resilient members disposed in third respective ones of the lumens, the two resilient members defining a plane of preferential bending of the deflectable segment when the manipulator changes an orientation of the deflectable segment.

4. The catheter according to claim 1, wherein at least one of the elongated members is coupled to the expandable distal end assembly, the manipulator being configured to deploy the expandable distal end assembly via the at least one elongated member.

5. The catheter according to claim 1, wherein the deflectable segment has an outside diameter of less than 3 mm.

6. The catheter according to claim 5, wherein each cable of the plurality of cables has an outside diameter of less than 0.5 mm and includes at least twenty insulated wires.

7. The catheter according to claim 6, wherein the plurality of cables comprises at least three cables.

8. The catheter according to claim 5, wherein each cable of the plurality of cables has an outside diameter of less than 0.5 mm and includes at least thirty insulated wires.

9. The catheter according to claim 8, wherein the plurality of cables comprises at least three cables.

10. The catheter according to claim 1, wherein each respective cable comprises tape which is wrapped around the bundle of insulated wires underneath the shielding.

11. The catheter according to claim 1, wherein the electrically insulating jacket includes any one or more of the following: polytetrafluoroethylene (PTFE); or perfluoroalkoxy alkane (PFA).

12. The catheter according to claim 1, wherein the deflectable segment comprises a thermoplastic elastomer.

13. The catheter according to claim 1, wherein the electrical shielding comprises a non-overlapping wire spiral.

14. The catheter according to claim 13, wherein the electrical shielding comprises a tinned-copper alloy.

15. The catheter according to claim 1, the expandable distal end assembly comprising:
   a first magnetic sensor disposed at a proximal end of the expandable distal end assembly; and
   a second magnetic sensor disposed at a distal end of the expandable distal end assembly.

16. The catheter according to claim 15, wherein the first magnetic sensor and the second magnetic sensor are configured to output one or more signals to a connected magnetic-sensing sub-system, the magnetic-sensing sub-system configured to determine an elongation or a retraction of the expandable distal end assembly based on a distance between the first magnetic sensor and the second magnetic sensor.

17. The catheter according to claim 16, wherein at least one of the first magnetic sensor and the second magnetic sensor comprises a triple-axis sensor.

18. The catheter according to claim 16, wherein the magnetic-sensing sub-system is further configured to estimate an ellipticity of the expandable distal end assembly based on the distance between the first magnetic sensor and the second magnetic sensor.

19. The catheter according to claim 1, wherein the lumens comprise a central lumen and a plurality of outer lumens surrounding the central lumen.

20. The catheter according to claim 19 further comprising a mechanical element extending through the central lumen and attached to a distal end of the expandable distal end assembly, the mechanical element configured to cause the expandable distal end assembly to transition between the expanded configuration and the collapsed configuration when actuated.

* * * * *